US011752024B2

(12) United States Patent
Ferrigolo et al.

(10) Patent No.: US 11,752,024 B2
(45) Date of Patent: Sep. 12, 2023

(54) ECCENTRIC AND POLYCENTRIC ARTICULATED TENSIONING JOINT FOR ORTHOPEDIC BRACES

(71) Applicant: F.G.P. S.R.L., Verona (IT)

(72) Inventors: Moreno Ferrigolo, Verona (IT); Alberto Turrini, Verona (IT)

(73) Assignee: F.G.P. S.R.L., Verona (IT)

( * ) Notice: Subject to any disclaimer, the term of this patent is extended or adjusted under 35 U.S.C. 154(b) by 338 days.

(21) Appl. No.: 17/254,993

(22) PCT Filed: Jun. 12, 2019

(86) PCT No.: PCT/IB2019/054912
§ 371 (c)(1),
(2) Date: Dec. 22, 2020

(87) PCT Pub. No.: WO2020/003040
PCT Pub. Date: Jan. 2, 2020

(65) Prior Publication Data
US 2021/0259870 A1  Aug. 26, 2021

(30) Foreign Application Priority Data
Jun. 25, 2018 (IT) .................. 102018000006628

(51) Int. Cl.
*A61F 5/01* (2006.01)
(52) U.S. Cl.
CPC .... *A61F 5/0125* (2013.01); *A61F 2005/0144* (2013.01)
(58) Field of Classification Search
CPC ............ A61F 5/0125; A61F 2005/0144; A61F 2005/0139; A61F 5/0123; A61F 5/37;
(Continued)

(56) References Cited

U.S. PATENT DOCUMENTS 5,921,946 A * 7/1999 Tillinghast ............ A61F 5/0123
602/26
9,668,903 B2 * 6/2017 Hsu ....................... A61F 5/0125
(Continued)

FOREIGN PATENT DOCUMENTS

WO    2017071863 A1   5/2017

OTHER PUBLICATIONS

Sulis, Elizabeth, International Search Report for PCT Application Serial No. PCT/IB2019/054912, dated Nov. 4, 2019, 5 pages.
(Continued)

*Primary Examiner* — Rachael E Bredefeld
*Assistant Examiner* — Eric Richard McQuiggan
(74) *Attorney, Agent, or Firm* — Ference & Associates LLC

(57) ABSTRACT

An eccentric and polycentric articulated tensioning joint applied to an orthopedic brace with adjustable angular excursion placed in correspondence of body joints comprises two bars each hinged to a rotation pin, wherein said rotation pins are constrained parallel to each other at a predefined distance, said two bars being connected to each other by means of respective semi-circular toothed profiles present on each bar, so as to be set in synchronous motion relative to each other. Said two bars are associated with a respective pair of loop elements, which are kinetically connected to said bars in such a way as to impart thereto the same rotational movements and partially transform them into relative translational movements along the longitudinal axes of each of the bars themselves, in order to effect linear movements of reciprocal distancing or nearing relative to the rotation centres thereof located on said pins.

5 Claims, 4 Drawing Sheets

(58) Field of Classification Search
CPC ...... A61F 2005/0137; A61F 2005/0167; A61F 5/04; A61F 5/042; A61F 5/00; A61F 5/0102; A61F 5/0106; A61F 2005/0132; A61H 3/00; A61H 2003/007; A61H 2201/1676; F16C 11/04
See application file for complete search history.

(56) References Cited

U.S. PATENT DOCUMENTS

| | | | | |
|---|---|---|---|---|
| 2011/0218470 A1* | 9/2011 | McCune | ................... | A61F 5/00 602/16 |
| 2014/0024978 A1* | 1/2014 | Killian | ................... | A61H 3/00 601/33 |
| 2015/0223958 A1* | 8/2015 | Dunn | ................... | A61F 5/0102 602/16 |
| 2015/0272768 A1 | 10/2015 | Chang | | |

OTHER PUBLICATIONS

Foged, Soren, Written Opinion of the International Searching Authority for PCT Application Serial No. PCT/IB2019/054912, dated Nov. 4, 2019, 5 pages.

* cited by examiner

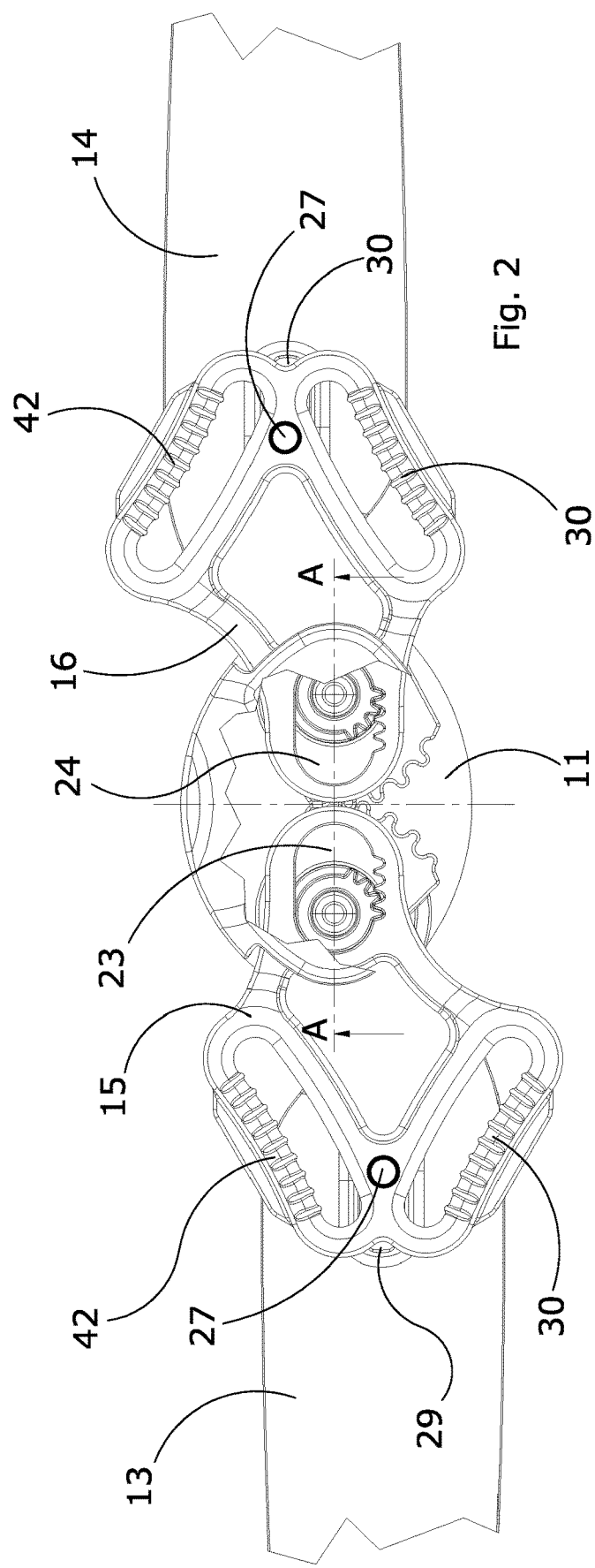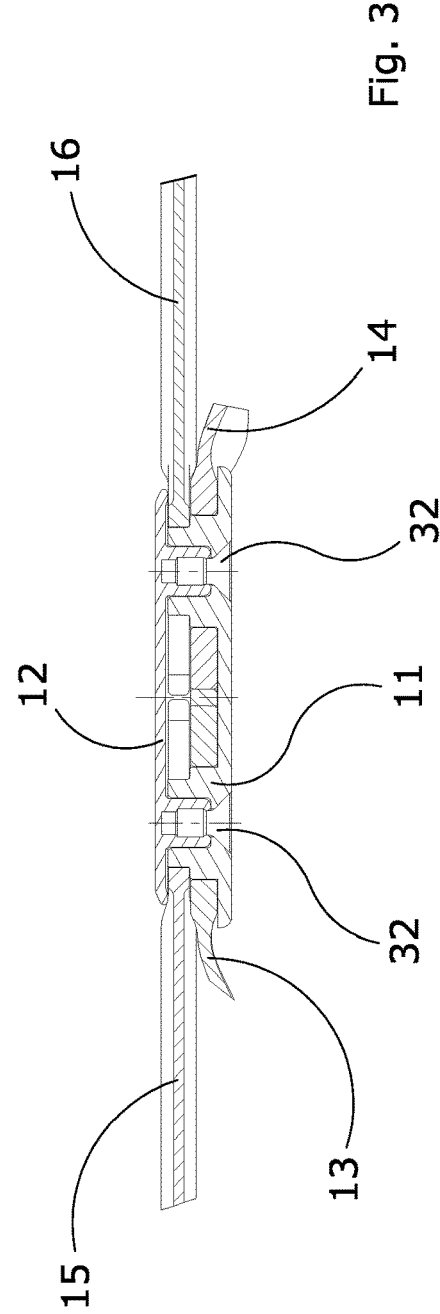

ECCENTRIC AND POLYCENTRIC ARTICULATED TENSIONING JOINT FOR ORTHOPEDIC BRACES

FIELD OF APPLICATION

The present invention relates to an eccentric and polycentric articulated tensioning joint for orthoses or orthopaedic braces designed for rehabilitation of joints of the human body, such as those of the knee, the elbow, the ankle, the shoulder or the like.

The eccentric and polycentric articulated tensioning joint according to the present invention relates to an articulated joint capable of setting two or more parts in rotation relative to a fixed part, with a variable distance relative to the centres of rotation, proportionally to the rotation made.

According to the invention it is in fact envisaged that the parts set in rotation, in addition to varying their angular position relative to the main axes of the fixed part, may also vary their relative distance from the centres of rotation located in predefined points of the fixed part.

It follows that the parts in rotation, irrespective of whether they are driven or driving parts, cause the total length of the entire system to vary according to the angle measured between the parts in rotation.

The present invention has application in the medical and orthopaedic fields, in particular in the manufacture of orthoses in general, as well as prostheses and braces mainly for use in conservative, post-traumatic, rehabilitative and postoperative therapy.

PRIOR ART

As is well known in the orthopaedic sector, in order to improve or aid the movement of limbs or joints debilitated by injuries or pathologies, use is made of so-called orthoses, also called orthopaedic braces, which are worn by individuals having orthopaedic problems with joints, such as the knee joint, as well as other joints such as the ankle or elbow joint, above all in the case of injuries or lesions or as a consequence of a previous surgical procedure.

In general, an orthopedic brace, or orthosis, is designed to ensure or control the function of a hinged constraint on the joints, for example between the femur and tibia in the case of the knee, but also other lever pivot points of joints, for example the elbow, by supporting stresses that would otherwise be damaging for the joint itself.

The function of an orthosis is, in general, to ensure a relative immobilization or limitation of a joint affected by injuries or arthritis or other pathologies, or by ligament sprains, or which has undergone a surgical procedure.

Another use of an orthosis is in conjunction with functional rehabilitation or re-education, where the orthosis can be used to reduce the load on a joint and decrease its pain, or be adopted for preventive purposes in cases of osteoporosis or bone yielding.

An orthosis usually consists of a rigid or soft frame encircling the limb and designed to ensure an adequate harnessing of the joint with the aim of preventing the occurrence of stress on the ligaments or synovial membranes when the injured and/or convalescing individual is walking.

According to the prior art, the frame of an orthosis for joints, for example in the typical case of a knee brace, comprises means of restraint on the femur and tibia and a section connecting said means, consisting of an articulated joint positioned at the level of the knee itself.

The means of restraint usually consist of preformed bars that are fixed by suitable straps which wrap around both the femur and tibia of the injured subject, or else bands, straps or sleeves made of fabric which enable a restraint to be created between the end of the mechanical articulated joint and the limb.

The mechanical articulated joint is positioned laterally relative to the femur and tibia, in the case of an example of application on the leg. Thanks to its configuration, consisting of two centres of rotation relatively constrained to each other thanks to toothed profiles, said articulated joint follows the kinematics of the knee with good approximation.

A standard polycentric articulated joint is a system made up of two hinged bars, each with its own centre of rotation, wherein said centres of rotation are constrained to each other in a parallel fashion and at a known distance.

In a standard polycentric articulated joint, the two bars are connected to each other thanks to a circular toothed profile present on each bar, and the toothed profile sets them in synchronous motion relative to each other.

In said articulated joint, by definition, the centres of rotation and the toothed profile make the bars able to rotate only about two parallel axes and their rotation motion thus lies in one plane.

Various solutions and types of articulated joints are used to correct different problems, for example articulated joints designed for use with special knee supports and braces intended also to correct any misalignments of the joint, generally through the use of spacers of various kinds inserted into the brace in proximity to the lateral thrust zone to be applied on the articulated joint.

Though they clinically and at least partially resolve the above-mentioned limb problems, the solutions in use to date are not devoid of problems, substantially tied to the use of the orthosis.

One drawback is represented by the fact that the joints of the human body, such as those of the knee, above all in the case of pathologies or other problems during walking, move in an irregular manner, that is, not exactly on one plane of rotation. Thus, traditional orthoses are not adequate for angular movements, since the parts set in rotation only vary their angular position relative to the main axes of the fixed part, it being impossible, given their constructive conception, for them also to vary their relative distance from the centre of rotation located in a precise point of the fixed part; it remains impossible for them to vary the total length of the entire system in following the anatomical movements of the limb.

It follows that such braces of a standard type, not being conceived to follow the anatomic variations in length that occur during the angular movement of joints, in actual fact lose adherence during movement of the limb, making it impossible for the orthosis to remain solidly secured to the limb itself, with the consequent loss of the function it is designed for.

Another drawback is represented by the fact that, again taking into consideration the knee joint, during movement, for example, while walking, it has been found that the tensions vary according to the position of the knee, which will tend to be overloaded in the angles ranging between 30° and 0° in extension, that is, in a sector in which the body's weight bears most on the joint, precisely in the moments in which it requires greater stability.

In order to remedy these problems, solutions have been conceived and realised which envisage using orthoses provided with an eccentric articulated tensioning joint realised according to a conception aimed at the possibility of setting two or more parts in rotation relative to a fixed part, with a variable distance relative to a single centre of rotation, proportionally to the rotation made.

This solution makes it possible for the parts in rotation, be they driven or driving parts, to bring about a variation in the total length of the entire system, according to the angle measured between the parts in rotation, for example in order to render the parts of a jointed orthopaedic brace more solidly secured to the part of the body it is applied on, so that it more appropriately follows the movement of a joint, which, by its very nature, tends to vary in length during its movement.

However, despite improving the work of the orthosis, this solution, too, has some limitations, in that the bars, which are connected to a single centre of rotation, can move freely, but must be guided by means of fastenings to the structure of the knee brace, or, for example, they must be sewn, attached with Velcro or inserted into special pockets, thus implying a certain laboriousness during the steps of production of the orthosis, which negatively impacts the costs of the finished product.

DESCRIPTION OF THE INVENTION

The present invention aims to provide an eccentric and polycentric articulated tensioning joint for orthoses or orthopaedic braces designed for rehabilitation of the knee or other orthopaedic braces applicable as aids for the joints of the human body, such as the knee, the ankle, the elbow or the like, and which is capable of eliminating or at least reducing the above-described drawbacks.

The invention further aims to provide an eccentric and polycentric articulated tensioning joint for orthoses or orthopaedic braces which is realised according to a conception aimed at still better stability of the orthosis, which can follow the movements of the joint in a more appropriate manner, using two or more parts in rotation relative to a fixed part having at least two centres of rotation, thus obtaining a polycentric articulated joint with double variable distances relative to the centres of rotation, proportionally to the rotation made.

This is achieved by means of an articulated joint for orthoses or orthopaedic braces designed for the rehabilitation of a limb, whose features are described in the main claim.

The dependent claims of the solution in question outline advantageous embodiments of the invention.

The main advantages of this solution relate above all to the fact that the parts of the articulated joint set in rotation, in addition to varying their angular position relative to the main axes of the fixed part, also vary their distance relative to the double centres of rotation located in very precise points relative to the fixed part.

Consequently, the parts in rotation, be they driven or driving parts, bring about a variation in the total length of the entire system, according to the angle measured between the parts in rotation, for example in order to render the parts of an articulated orthopaedic brace more solidly secured to the part of the body on which it is applied, so that it follows the movement of a joint, which by its very nature tends to vary in length during its movement, in a more appropriate manner.

Another use of this articulated joint relates to its function of varying the traction of the straps for containing a joint as the instability of the joint itself varies.

This aspect is decisive for the correction of joints affected by varus or valgus angles exceeding physiological limits.

One example regards the case of the knee joint, where tensioning of the straps, which increases with increases in the extension of the leg (and thus of the articulated joint), brings about a corrective effect on a varus/valgus misalignment of the joint itself.

If the articulated joint is placed laterally to the joint, it will exert an anti-varus force upon the latter, which will bring the femur and tibia back into correct alignment, in order to ensure correct walking. If, on the other hand, the articulated joint is placed on the medial side of the knee, it will exert an anti-valgus thrust that will realign the knee joint in the opposite direction.

One of the advantages obtained by the invention regards the fact that the kinematics of the articulated joint more faithfully replicate the kinematics of the knee, thus achieving optimal operating functionality and comfort for the user.

Further advantages regard the symmetry of the angular movement of the two bars relative to the central body of the articulated joint, which prevents the need for fastenings to the structure of the orthosis, as compared to a present condition, which is worse, since the bars can move freely relative to a single centre, but must be guided by means of fastenings to the structure of the knee brace, for example sewn, or attached by Velcro or inserted in special pockets.

The articulated joint according to the invention offers a further advantage compared to traditional solutions, due to the fact that the articulated joint has a thinner profile, since the parts making it up are distributed over two centres of rotation and no longer aligned along a single axis.

An important aim achieved by the invention regards the fact that the bars, having a symmetrical angular motion relative to the central body, enable the upper and lower straps to be tensioned in an equal manner.

ILLUSTRATION OF THE DRAWINGS

Other features and advantages of the invention will become more apparent on reading the following description of an embodiment of the invention, provided by way of non-limiting example with the aid of the drawings illustrated in the attached figures, in which:

FIG. 2 illustrates a detailed plan view of the eccentric and polycentric articulated tensioning joint according to FIG. 1;

FIG. 3 illustrates a detailed sectional view of the articulated joint according to the invention, according to the line A-A of FIG. 2;

Figure 4:
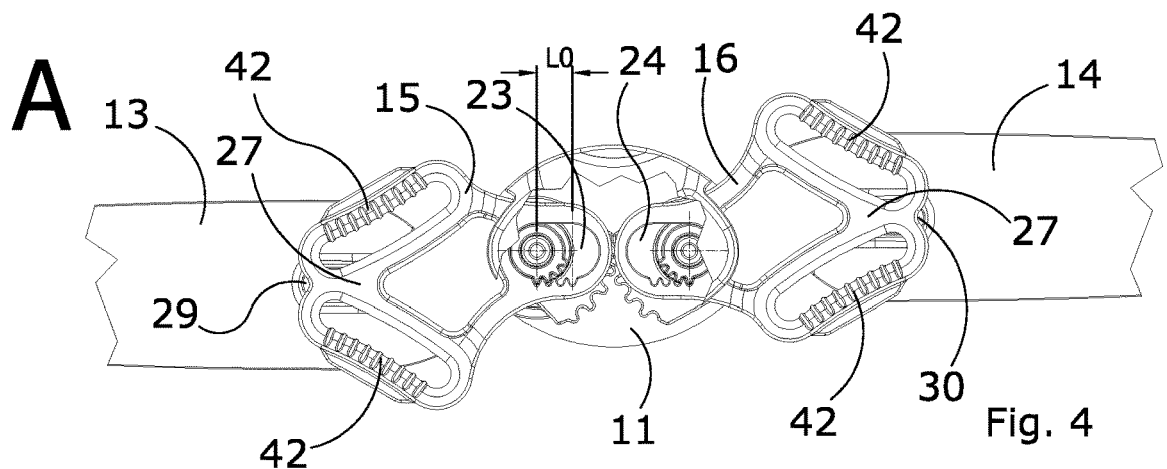
Figure 5:
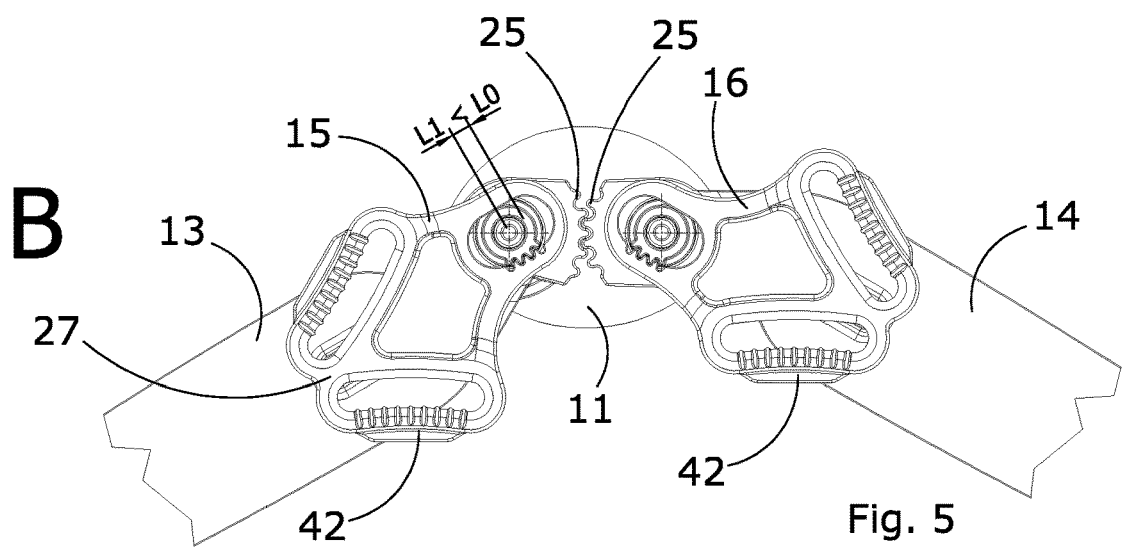
Figure 6:
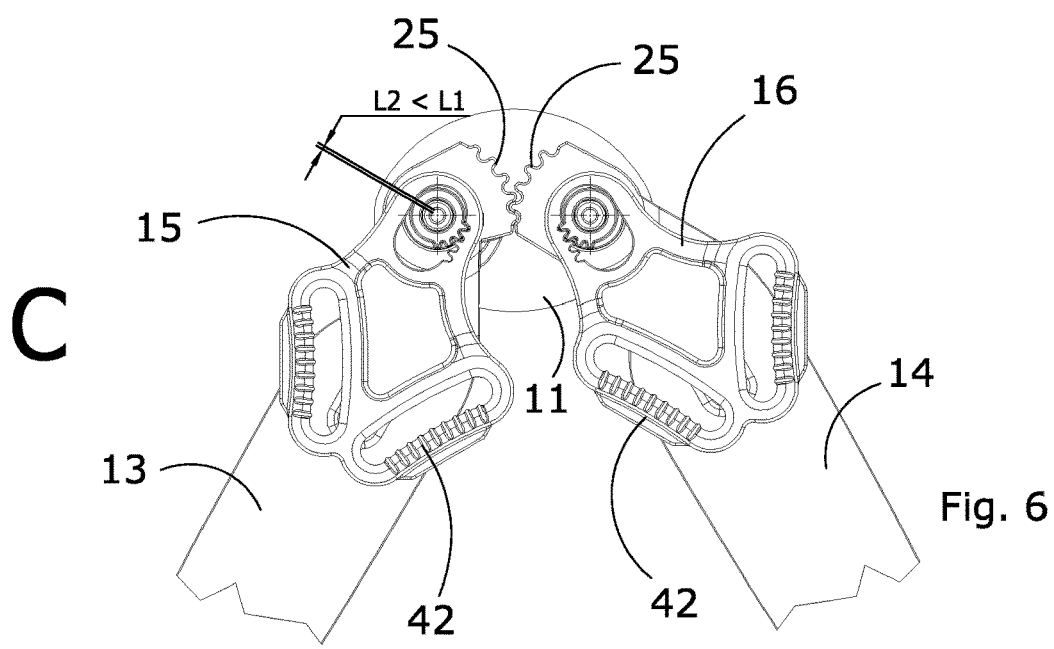
Figure 7:
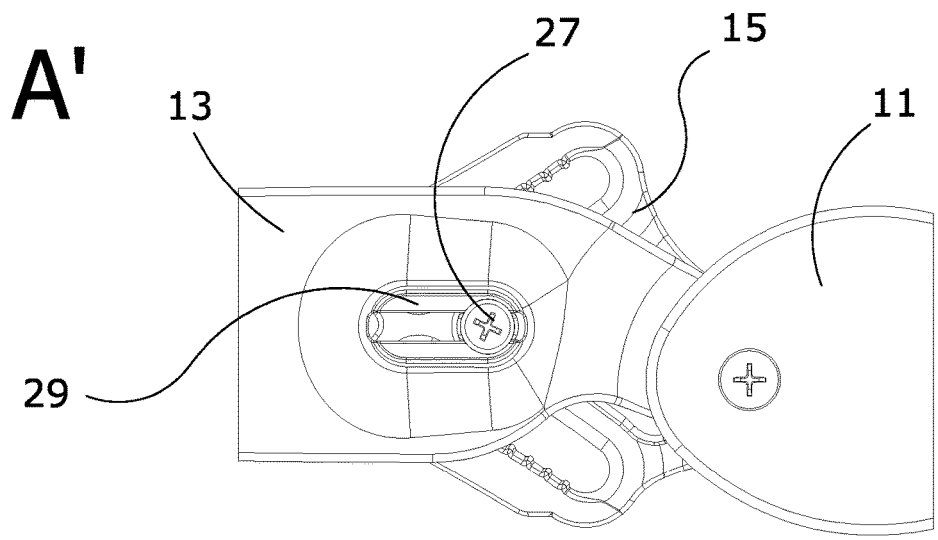
Figure 8:
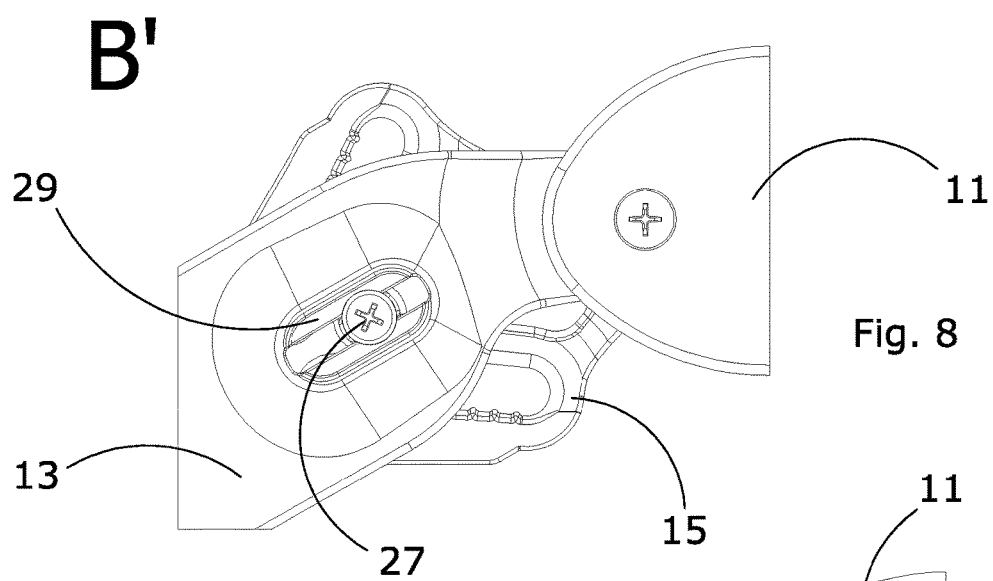
Figure 9:
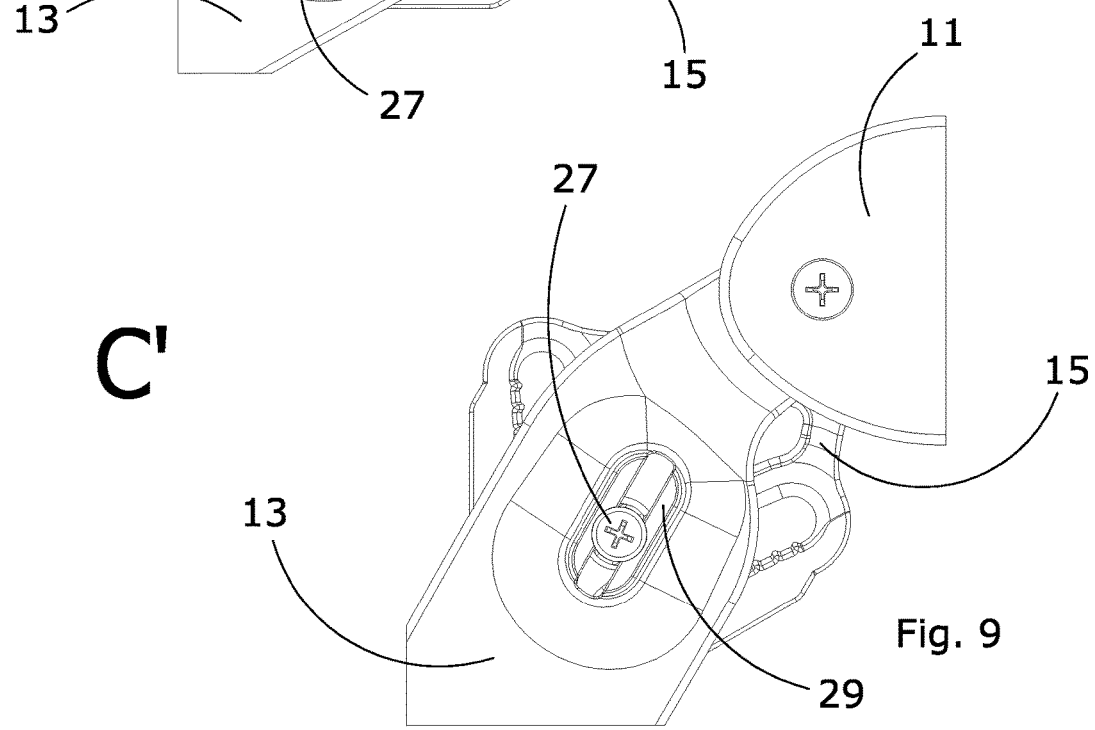

FIGS. 4, 5 and 6 represent views of the articulated joint according to the invention with the angles disposed, respectively, at 0°, in an intermediate position around 30° and in a position with a more acute angle of around 60';

FIGS. 7, 8 and 9 illustrate views of a detail of the articulated joint in three different angular positions, 0°, 30° and 60°, respectively.

DESCRIPTION OF AN EMBODIMENT OF THE INVENTION

Figure 1:
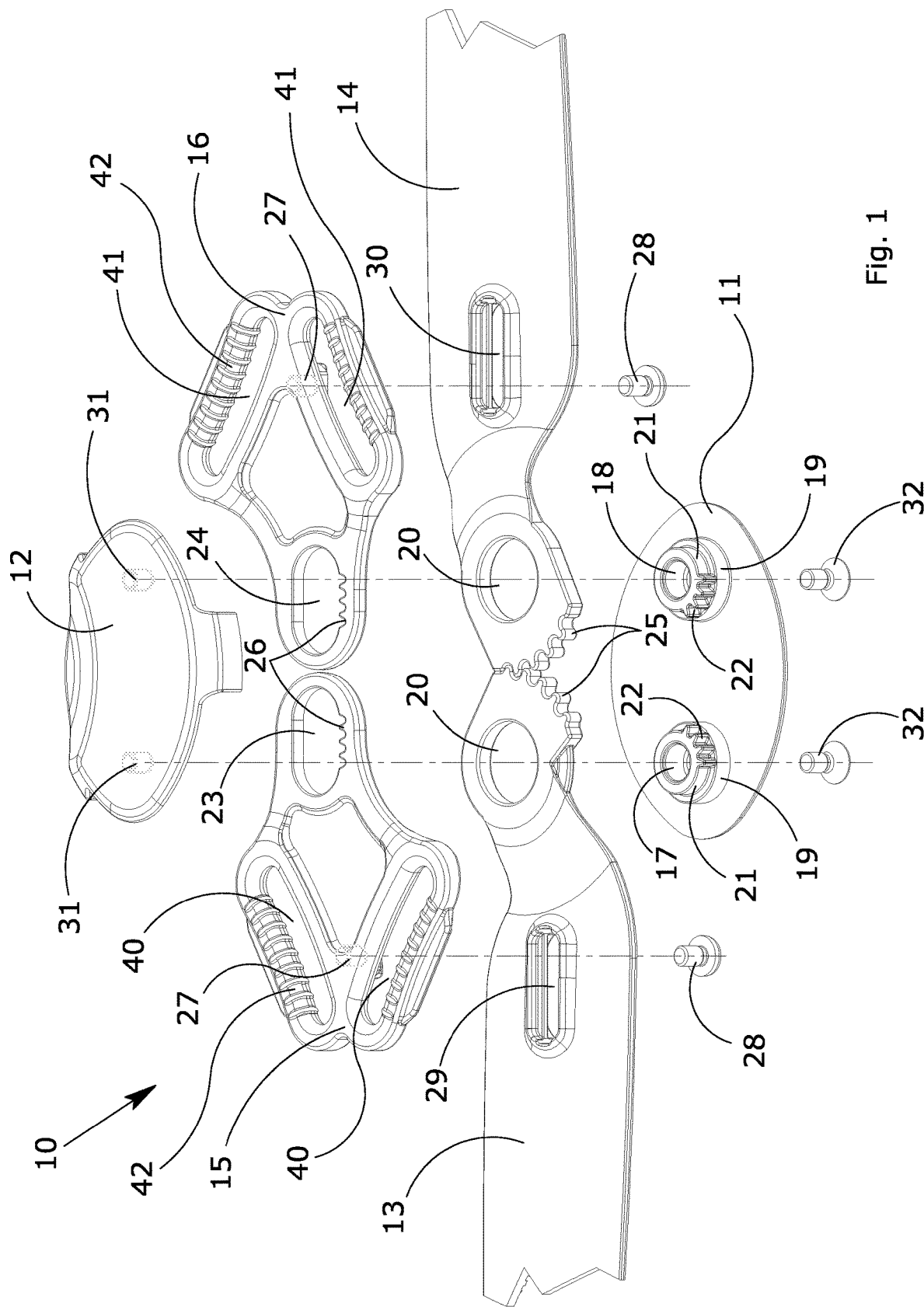
FIG. 1 represents an exploded view of an eccentric and polycentric articulated tensioning joint according to the invention.

Making reference initially to FIG. 1, the number 10 denotes in its entirety an eccentric and polycentric articulated tensioning joint for an orthopaedic brace to be applied on the joints of the human body, with a controllable angular excursion.

The articulated joint 10 according to the invention comprises a base structure made up of two substantially discoid connecting elements 11 and 12 having an approximately rounded or elliptical shape or another more appropriate shape, also depending on the area of application and the type of joint to be treated and upon which it is intended to rest, such as, for example the knee, or elbow, or another joint, which are intended to be reciprocally coupled so as to comprise within them the ends, which are joined, of a first pair of coplanar jointed bars 13 and 14, each of which is provided with a circular bored end 20, and a second pair of double coplanar jointed loop elements 15 and 16, each of which is provided with a slot-shaped bored end 23, 24 internally provided with a portion provided with teeth 26.

More precisely, making reference initially to the embodiment in FIG. 1, the discoid element 11 is internally provided with a pair of circular pins 17 and 18, each of which is made in two bodies positioned on two levels: a first circular-shaped lower body 19 positioned against the discoid element 11 and intended to receive the circular bored ends 20 of the two bars 13 and 14 and a second body 21, in part smooth and in part having teeth 22, intended to receive the elongate slot-shaped bored ends 23 and 24 of the double jointed loop elements 15 and 16.

Each of the jointed loop elements 15 and 16 is provided with a pair of strap loop slots, indicated as 40 in the case of the first one and 41 in the case of the second one, which are disposed relative to each other according to a predefined angle so as to cooperate correctly with a further articulated joint on the other side of the brace.

The strap loop slots 40 and 41 are located on the inside of knurled edges 42 of the respective loop elements, which cooperate for the stabilisation of the tensioning movements of the straps.

The facing ends of the two bars 13 and 14 are provided with teeth 25 disposed so as to reciprocally mesh, so that the rotation of one corresponds to the equal and symmetrical rotation of the other.

Moreover, the elongate slot-shaped perforations 23 and 24 of the double loop elements 15 and 16 are likewise provided with teeth 26 which mesh with the aforesaid teeth 22 of the pins 17 and 18.

Finally, said double coplanar jointed loop elements 15 and 16 are provided with seats 27 in which screws 28 are inserted, passing through the slot-shaped openings 29 and 30 fashioned, respectively, on each of the bars 13 and 14, in which the screws themselves can slide, as will be seen below, while the substantially discoid outer elements 12 are provided with small projecting bored cylinders 31 intercepted by screws 32 which pass through the pins 17 and 18 so as to tighten the articulated joint and enable the use thereof.

The assembly of the articulated joint entails the introduction of the two bars 13 and 14 into the pins 17 and 18 so that the circular holes 20 are inserted into the first smooth body 19 of the support 11, the introduction into the same pins 17 and 18 of the double jointed loop elements 15 and 16, whose bored ends 23 and 24 will be disposed in proximity to the second body 21, the connection, by means of the screws 28, between the double jointed loop elements 15 and 16 of the two bars 13 and 14 which constrain the rotation, leaving the same screws 28 and the loop elements connected to them free to slide in the slot-shaped openings 29 and 30, and the closure of the whole with the introduction of the discoid support 12, so that the respective small projecting bored cylinders 31 can be intercepted by the screws 32 which pass through the pins 17 and 18, so as to reach the assembly represented in FIGS. 2 and 3.

From an operational viewpoint, the functional principle of the articulated joint according to the invention is based on the angular movement which is synchronised between the two opposing bar/jointed loop element groups making up each pin 17 and 18, with the loop elements 15 and 16 being free to slide in a longitudinal direction on the respective bars 13 and 14 along the slot-shaped openings 29 and 30.

As represented in FIGS. 4 to 6 and 7 to 9, the angular movements of the bar 13 and the jointed loop element 15 mirror and are symmetrical relative to the angular movements of the bar 14 and the jointed loop element 16, since the two bars 13 and 14 mesh reciprocally on the toothed ends 25 and the same two bars 13 and 14 are constrained to the respective jointed loop elements 15 and 16, which in turn comprise the bored ends 23 and 24 provided with teeth 26 which mesh with the teeth 22 of the pins 17 and 18; the result is not only the symmetry of the angular movements of the bars and loop elements, but also the sliding of the jointed loop elements 15 and 16 nearer to or away from their centres of rotation, due to the sliding of the pins 28 along the slots 29 and 30 while the teeth 26 are meshed with the teeth 22 of the pins 17 and 18.

The angular movement of the bars 13 and 14 relative to the pins 17 and 18 brings about the angular movement of the double loop elements 15 and 16 and the simultaneous translation thereof along the same bars 13 and 14, thus enabling the reciprocal distancing or nearing thereof from or to the respective centres of rotation.

In particular, the distancing of the loop elements 15 and 16 is brought about during bending of the bars, and the nearing thereof is brought about when the bars tend towards their longitudinal alignment.

Said distancing or nearing movements of the double loop elements 15 and 16 relative to the pins 17 and 18 bring about, respectively, the release or tensioning of the straps which pass through the openings 40 of the loop elements themselves and which are constrained on the opposite sector of the joint, with a consequent better stability of the orthosis.

As already noted previously, the function of the articulated joint according to the invention is to vary the traction of the straps containing a joint as the instability of the joint itself varies, considering that such variation is decisive for the correction of joints affected by varus or valgus angles exceeding physiological limits.

In the specific case of the knee joint, the tensioning of the straps, which increases with increases in the extension of the leg (and thus of the articulated joint), brings about a corrective effect on a varus/valgus misalignment of the joint itself.

If the articulated joint is placed laterally to the joint, it will exert an anti-varus force which will bring the femur and tibia back into correct alignment, in order to ensure correct walking. If, on the other hand, the articulated joint is placed on the medial side of the knee, it will exert an anti-valgus thrust that will realign the knee joint in the opposite direction.

The invention has been described above with reference to a preferred embodiment thereof. However, it is clear that the invention is susceptible of numerous variants falling within the scope thereof, within the framework of technical equivalences.

The invention claimed is:

1. An eccentric and polycentric articulated tensioning joint for an orthopaedic brace with adjustable angular excursion to be placed in correspondence of body joints of a user, comprising two bars, each hinged to a respective rotation pin placed on an element of a base structure, two bars being connected to each other by means of respective toothed profiles provided at a circular end of each bar, so as to be set in synchronous motion relative to each other, further comprising a pair of loops, wherein each loop comprises two elongate slot-shaped strap loop elements positioned relative to each other at a predetermined angle, as well as an elongate bored end comprising first teeth which the respective rotation pin is inserted in, the pin further comprising second teeth (22) cooperating with the first teeth, whereby each bar comprises an elongate opening allowing a shank of a screw element which connects one of the bars to one of the loops, to slide inside it, so that the movement of reciprocal rotation of the bars results in a translational movement of respective approaching or moving away of said loops.

2. The articulated joint of claim 1, wherein the base structure comprises two opposing discoid elements which are reciprocally coupled to include the circular ends of the bars and the pair of loops attached to thereto.

3. The articulated joint of claim 2, wherein each rotation pin comprises a first circular-shaped lower body positioned on one of the two opposing discoid elements and receives a circular end of one of the two bars, and a second upper body, a part of which is smooth and another part of which has the second teeth which receive the elongate bored end of one of the respective loops.

4. The articulated joint of claim 2 wherein the discoid elements comprise small projecting bored cylinders intercepted by screws which pass through the respective rotation pins to enable tightening of the articulated joint.

5. The articulated joint of claim 1, wherein the elongate slot-shaped strap loop elements are located on the inside of knurled edges provided on the respective loops the knurled edges acting for a stabilisation of tensioning movements of straps connected to the brace.

\* \* \* \* \*